United States Patent
D'Andrea

(10) Patent No.: US 10,207,127 B2
(45) Date of Patent: Feb. 19, 2019

(54) RADIATION TREATMENT SHEET DEVICES AND METHODS

(71) Applicant: Mark A. D'Andrea, Houston, TX (US)

(72) Inventor: Mark A. D'Andrea, Houston, TX (US)

(*) Notice: Subject to any disclaimer, the term of this patent is extended or adjusted under 35 U.S.C. 154(b) by 179 days.

(21) Appl. No.: 15/439,008

(22) Filed: Feb. 22, 2017

(65) Prior Publication Data

US 2017/0157421 A1 Jun. 8, 2017

Related U.S. Application Data

(63) Continuation of application No. 13/843,099, filed on Mar. 15, 2013, now Pat. No. 9,604,074.

(51) Int. Cl.
*A61N 5/02* (2006.01)
*A61N 5/10* (2006.01)
(Continued)

(52) U.S. Cl.
CPC ........... *A61N 5/1028* (2013.01); *A61N 5/025* (2013.01); *A61N 5/1029* (2013.01);
(Continued)

(58) Field of Classification Search
CPC .................. A61N 5/0625; A61N 5/025; A61N 2005/1012; A61N 5/1018; A61N 5/1001–5/1029; A61F 2007/0091–2007/0092; A61F 2007/0201–2007/108; A61F 2007/0001–2007/0052; A61F 7/02–7/106
(Continued)

(56) References Cited

U.S. PATENT DOCUMENTS 2,566,533 A * 9/1951 Poux ..................... A61F 7/02
156/146
2,829,636 A 4/1958 Henschke
(Continued)

OTHER PUBLICATIONS

Horton, John et al., LDR Intracavitary Brachytherapy Applicators, UT MD Anderson Cancer Center Intracavitary Brachytherapy, 2005.
(Continued)

*Primary Examiner* — Catherine B Kuhlman
(74) *Attorney, Agent, or Firm* — Cook Alex, Ltd.

(57) ABSTRACT

Radiation therapy devices, systems and methods are in general sheet-like form, are characterized by flexibility, and include at least one spacer that can be a balloon or bubble that assists in placement of radio therapeutic members at desired treatment locations along or around a limb, within an existing body cavity, or at a site that was formed under a patient's skin for treatment purposes. Sarcoma treatment is particularly conducive to treatment by these devices, systems and methods. One or more detectors, such as microdiodes, are accommodated when desired on the device, and a hyperthermia tube or the like is also includable that delivers hyperthermia treatment for the target treatment site or sites. Data collected by the detector allows the medical professional to monitor radiation treatment and, when desired, interaction between hyperthermia treatment and radiation delivery by the radiation treatment member.

21 Claims, 11 Drawing Sheets

(51) Int. Cl.
*A61B 18/00* (2006.01)
*A61N 7/02* (2006.01)
*A61N 7/00* (2006.01)
*A61B 90/00* (2016.01)

(52) U.S. Cl.
CPC .............. *A61N 5/1071* (2013.01); *A61N 7/02* (2013.01); *A61B 2018/0025* (2013.01); *A61B 2090/036* (2016.02); *A61N 7/00* (2013.01); *A61N 2005/1018* (2013.01)

(58) Field of Classification Search
USPC ..................................... 607/96–114; 600/1–8
See application file for complete search history.

(56) References Cited

U.S. PATENT DOCUMENTS

| | | | |
|---|---|---|---|
| 3,060,924 A | 10/1962 | Rush | |
| 3,587,578 A * | 6/1971 | Walker | A61F 7/02 604/304 |
| 3,861,380 A | 1/1975 | Chassagne et al. | |
| 4,294,264 A | 10/1981 | Fischell et al. | |
| 4,323,055 A | 4/1982 | Kubiatowicz | |
| 4,434,789 A | 3/1984 | Kumar | |
| 4,631,415 A | 12/1986 | Sauerwein et al. | |
| 4,714,445 A * | 12/1987 | Templeton | A61F 7/02 446/369 |
| 4,733,653 A | 3/1988 | Leung et al. | |
| 4,861,520 A | 8/1989 | van't Hoft et al. | |
| 4,881,937 A | 11/1989 | van't Hooft et al. | |
| 4,881,938 A | 11/1989 | van't Hooft et al. | |
| 4,886,063 A * | 12/1989 | Crews | A61F 7/02 607/112 |
| 4,897,076 A | 1/1990 | Puthawala et al. | |
| 4,969,863 A | 11/1990 | van't Hooft et al. | |
| 5,012,357 A | 4/1991 | Schoeppel et al. | |
| 5,090,043 A | 2/1992 | Parker et al. | |
| 5,106,360 A | 4/1992 | Ishiwara et al. | |
| 5,306,271 A | 4/1994 | Zlnreich et al. | |
| 5,520,646 A | 5/1996 | D'Andrea | |
| 5,653,683 A | 8/1997 | D'Andrea | |
| 5,720,717 A | 2/1998 | D'Andrea | |
| 5,913,813 A | 6/1999 | Williams et al. | |
| 6,312,375 B1 | 11/2001 | Montebello et al. | |
| 6,413,204 B1 | 7/2002 | Winkler et al. | |
| 6,482,142 B1 | 11/2002 | Winkler et al. | |
| 6,699,171 B2 | 3/2004 | Harmon | |
| 7,534,202 B2 | 5/2009 | Eng | |
| 7,556,596 B2 | 7/2009 | Mourtada et al. | |
| 7,651,458 B2 | 1/2010 | Mourtada et al. | |
| 7,666,130 B2 | 2/2010 | Mick | |
| 8,033,979 B2 | 10/2011 | Mick | |
| 8,876,684 B1 | 11/2014 | Nakaji | |
| 2003/0153803 A1 | 8/2003 | Harmon | |
| 2004/0006305 A1 | 1/2004 | Hebert et al. | |
| 2004/0039432 A1 | 2/2004 | Warriner | |
| 2005/0251235 A1 * | 11/2005 | Schlorff | A61N 1/403 607/101 |
| 2006/0100475 A1 | 5/2006 | White et al. | |
| 2006/0116546 A1 | 6/2006 | Eng | |
| 2010/0145132 A1 | 6/2010 | Isham | |

OTHER PUBLICATIONS http://www.cancer.org/Treatment/TreatmentsandSideEffects/TreatmentTypes/hyperthermia, Downloaded May 2, 2012.
Research Spotlight, Eos, vol. 92, No. 33, Aug. 16, 2011.
Zhu, Timothy C., Diode Dosimetry for Megavoltage Electron and Photon Beams, Dept. of Radiation Oncology, U. of Pennsylvania, Philadelphia, PA, Jun. 24, 2009.
Dutta, Pinaki, MD et al., How is radiation therapy given?, OncoLink Cancer Resources, www.oncolink.org/treatment/article, Downloaded Oct. 28, 2011.
http://vantageoncology.com/centers2006/html/body/treatment/wildomar, High-Dose Rate Brachytherapy (HDR)TandemandOvoid Implant, WildomarRadiationTherapyCentr, DownloadOct. 31, 201.
www.americanbrachytherapy.org/aboutBrachytherapy,What is Brachytherapy?, American Brachytherapy Society, Downloaded Nov. 4, 2009.
Section III: Disease Sites, Chapter 22: Uterine Cervix, textbook pp. 657-659, circa 2001.
Corrao, Anita, MS, CMA, DABRE, A comparison of APBI brachytherapy techniques: MammoSite . . . , Lifespan, Providence, RI, 2010.
MicroSelectron—body site applicator solutions, Oncoselect by Nucletron, circa Mar. 2010.

\* cited by examiner

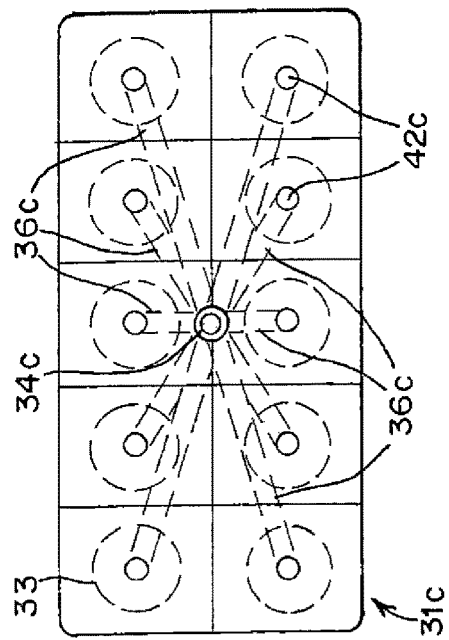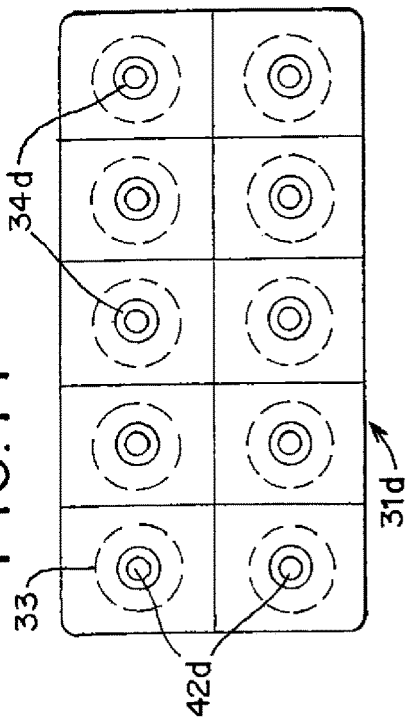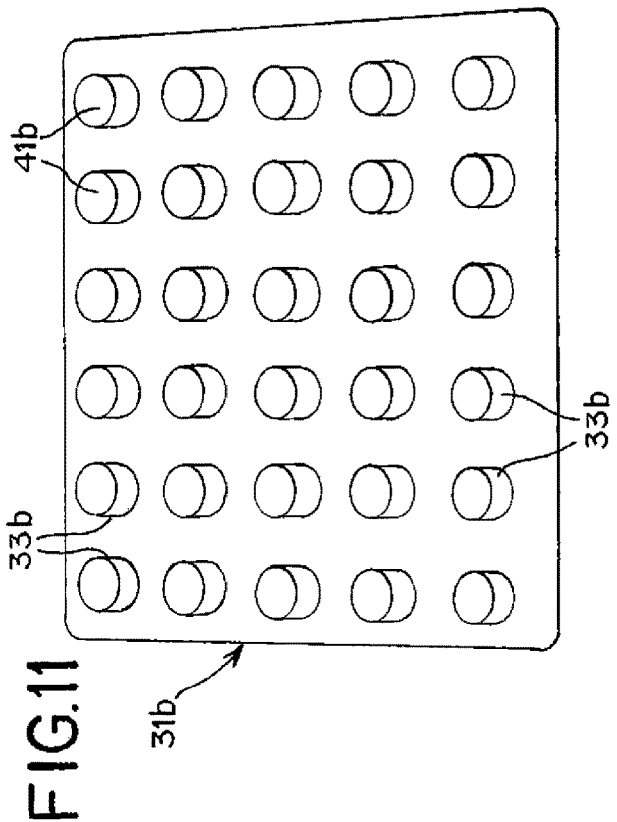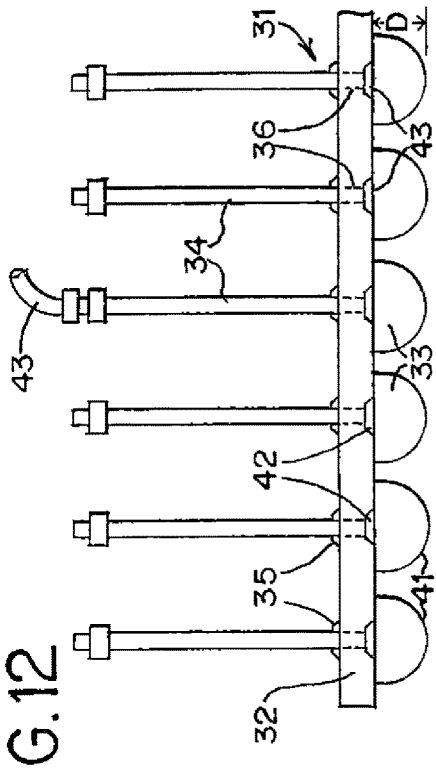

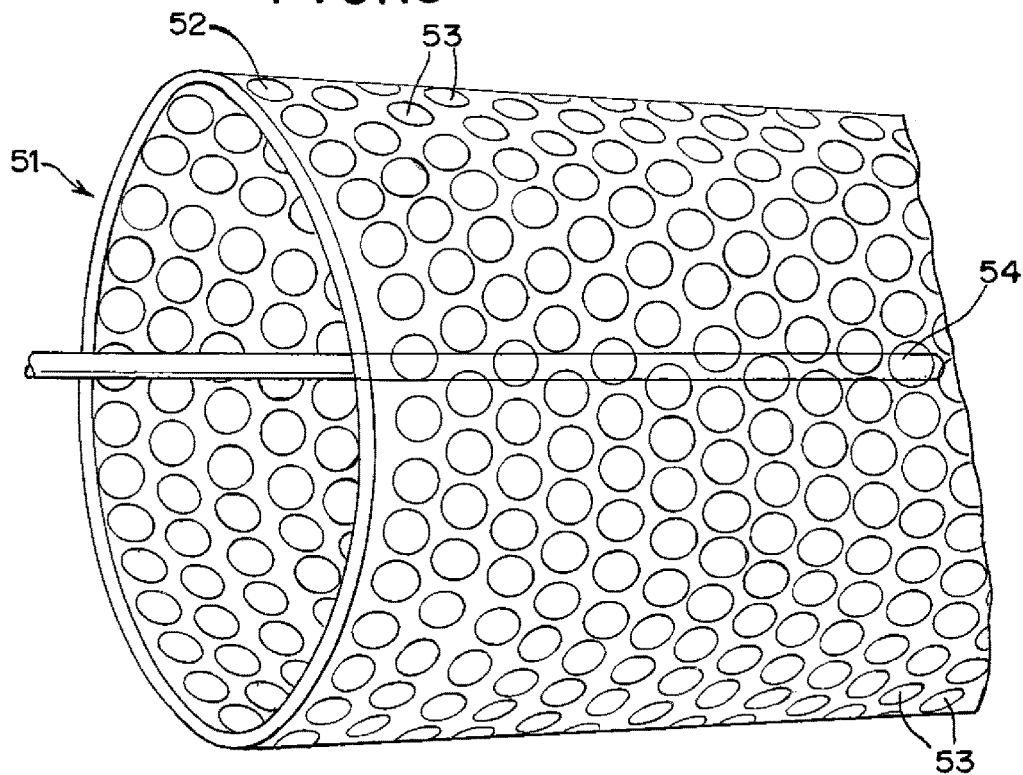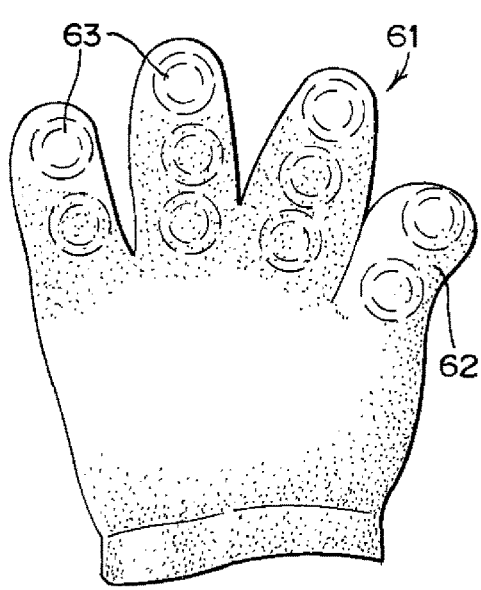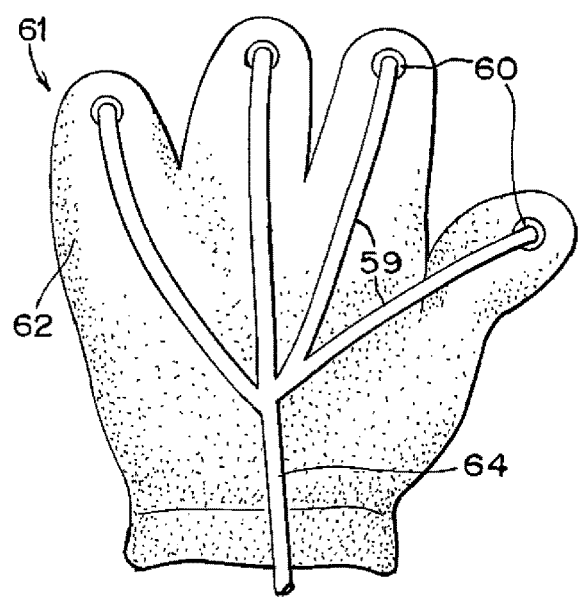

RADIATION TREATMENT SHEET DEVICES AND METHODS

This application is a continuation of and claims the benefit of U.S. application Ser. No. 13/843,099, filed Mar. 15, 2013, hereby incorporated by reference hereinto.

TECHNICAL FIELD

The present subject matter relates to systems, devices and therapeutic procedures used during radiation treatment. The field encompasses radiation oncology procedures with respect to a wide variety of cancerous conditions specifically including sarcomas. Radioactive material is delivered by implements incorporating an array that is somewhat flexible and able to conform to varying degrees depending on body locations in need of radiation therapy.

BACKGROUND

Radiation oncology practitioners and researchers have developed various devices, systems and methods, each typically being designed for a specific diseased body organ or part and/or for one or more treatment regimens. Whether the treatment regimen is a one-step or multi-step protocol, it is important to maintain a good balance among radiation dosage, placement and timing. Timing can involve treatment and non-treatment intervals that vary depending upon the oncology protocol to be followed.

Carcinoma and sarcoma treatment procedures can follow a protocol calling for a series of multiple applications, such as when following high dose rate (HDR) brachytherapy. At times, the radiation oncologist may choose to use a low dose rate (LDR) regimen, typically based on cesium delivery as $^{137}Cs$. For HDR regimens $^{192}Ir$ is frequently used because of its high specific activity. Other isotopes are available and used as warranted. The degree of treatment is measured in terms of units of radiation exposure (in roentgens or Gray or Gy), and often these are prescribed at specific points. Details in this regard are known to radiation oncologists, medical physicists and other medical professionals experienced in the art. An objective often is to provide reasonably constant and predictable dose rates at each location at which the isotopes are applied.

Sarcomas are types of cancer that develop from certain tissues, usually bone or muscle. Bone sarcomas are generally thought of as bone cancer. Soft tissue sarcomas develop from soft tissues such as fat, muscle, nerves, fibrous tissues, blood vessels, deep skin, cartilage, and hematopoietic tissues. For example, osteosarcoma arises from bone, chondrosarcoma arises from cartilage, liposarcoma arises from fat, and leiomyosarcoma arises from smooth muscle. Some sarcomas are evident, being on skin surface, while others are internal and require surgical procedures to access the sarcoma for surgery, radiation therapy or a combination thereof. Efforts have been made to advance targeted therapy treatment.

Sarcoma cancers can be found in any part of the body, although many of them develop in arms or legs. Less commonly, sarcomas also can be found in the trunk, head and neck area. Sarcomas are also experienced with internal organs and areas in the back of the abdominal cavity.

Radiation therapy for soft tissue sarcomas can be addressed with external beam radiation therapy or brachytherapy. In external beam radiation therapy, radiation is delivered from outside the body and focused on the cancer, and this is typical radiation therapy applied to treat sarcomas. These can include intensity modulated radiation therapy (IMRT) and proton beam radiation. Brachytherapy or internal radiation therapy places small pellets or seeds of radioactive material in or near the cancer. Traditionally, for soft tissue sarcoma, the pellets or seeds are put into catheters that have been placed during surgery. Because of side effects, it is important that radiation therapy proceed with precision, including enhanced assurance of proper placement with respect to the cancerous site, whether relatively small or larger. At times, sarcomas cover a relatively large surface area.

Accordingly, it is clear that body surface radiation treatment and other treatments such as those gaining access through a surgical opening or access location, need to be exacting and specific in each of dose rates, durations and radiation target locations, for example. In addition, the closeness of tissue not intended to be irradiated should be taken into consideration. For example, the present disclosure has come to recognize that the radiation oncologist may find it useful to have adequate direct control in isotope placement to generate a radiation treatment plan specific for this placement and for the particular anatomy and disease location and severity for the particular patient and for the treatment event at hand.

It will be appreciated that radiation delivery systems can be used in treatments that are applied manually or remotely using remote afterloading systems. In remote afterloading systems, the radioactive materials are delivered from a source by way of hollow tubes to hollow treatment portions or locations. Radioactive material can be in the form of wires, seeds, fluids or other forms.

SUMMARY

There are several aspects of the present subject matter that may be embodied separately or together in the systems, devices and methods described herein and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, systems, devices and methods are provided for body surface radiation therapy with a disposable sheet-type component having an array of elongated balloons and/or generally spherical to hemi-spherical bubbles and/or porous or non-traumatic spaces that space the target site a proper distance from the sources of radiation dose delivery.

In another aspect, the subject matter relates to therapeutic procedures, systems and devices used during radiation therapy and that incorporate an array of radio therapeutic delivery terminus points on a support that exhibits adequate flexibility to allow the medical professional to generally conform the array to a diseased body surface. Radio therapeutic members, tubes or elongated rods for containing radioactive material engage the delivery terminus points to connect with a remote isotope source. Importantly, a balloon or inflated bubble is positioned between the delivery terminus points and the body surface to be treated. Microdiodes can be incorporated to achieve real-time treatment and analysis capabilities, and hyperthermia components can be included.

In another aspect, a sheet-form assembly is a support for one or more therapeutic delivery terminus points accessible to radiation source material from one face of the sheet-form assembly while an inflated or inflatable member is on its opposite face. In another embodiment, the support itself is inflatable. Sheet flexibility facilitates proper radiation treatment position for a body surface or within a surgery site during radiation therapy. The sheet-form assembly, particularly if an inflatable component is included, also may be used to move, push, reposition, hold or otherwise manipulate body tissue prior to and during the radiation therapy. Radioactive solutions can be provided in the delivery terminus points, and microdiodes and hyperthermia channels can be incorporated.

In yet a further aspect, a sheet-form assembly is shaped like a glove, partial glove, mitten, finger sleeve, digit band or foot clog. Such sheet-form assembly is a support for one or more radiation delivery tubes or therapeutic delivery terminus points, accessible to radiation source material from one face of the sheet-form assembly while an inflated member is on its opposite face. Sheet flexibility facilitates proper radiation treatment position for a body surface or within a surgery site during radiation therapy. The sheet-form assembly also may be used to move, push, reposition, hold or otherwise manipulate body tissue prior to and during the radiation therapy. Radioactive solutions can be provided in the radiation delivery tubes or delivery terminus points, and microdiodes and hyperthermia channels can be incorporated.

In another aspect, the physician is provided with the equipment and techniques for treating a variety of sarcoma cancers, whether on a body surface or through a surgically made opening, including at retroperitoneum locations. Treatment can continue while the device is positioned and later retrieved or removed, typically depending on the treatment protocol being followed. Catheter-type channels are used for delivery of radioactive material and balloons, bubbles or other atraumatic spacers are interposed to provide adequate spacing from the treatment site. Microdiodes can be incorporated to achieve real-time treatment capabilities, and hyperthermia components can be included.

In a further aspect, the radiation treatment device, system and method include at least one radiation delivery channel or tube that feeds a plurality of treatment sites of a flexible sheet-like member that folds or curls or rolls onto itself. In other embodiments, multiple tubes, rods or catheters are provided, one for each treatment site terminus. In other embodiments, a plurality of delivery tubes, rods or catheters feed a grouping of radiation treatment terminus sites, and multiple groupings are provided on the sheet-like support surface. In each situation, the support surface has a certain degree of flexibility by which the medical professional can shape or fashion the substrate and hence the radiation treatment terminus sites or points in order to better coincide with the topography of the sarcoma or other cancer.

Another aspect facilitates long-term, low dose rate radiation by enabling introduction of nutrients or gassed or evacuation of wastes and/or gasses through a component of the therapeutic treatment device. Catheter-type channels can be used for delivery of radioactive solids or solutions to locations safely spaced from target treatment sites. Diodes or microdiodes can be incorporated to achieve real-time treatment capabilities, and hyperthermia components can be included.

Another aspect permits the physician to tailor the size and shape of a radiation treatment device to the particular therapeutic requirements of the body surface or topography being treated. One or more catheter-type channels deliver radioactive material, safely spaced by inflated longitudinal balloons, bubbles or other atraumatic spacers. On a non-removable or removable basis, microdiodes can be incorporated to achieve real-time treatment and monitoring capabilities, and non-removable or removable hyperthermia components can be included. In embodiments, inflatable components (for example balloons or the flexible support of the device) are added to shield areas not to be treated and/or to manipulate body tissue or organs prior to and during radiation treatment. Other embodiments have the inflatable member coincide with the atraumatic spacers.

In a further embodiment, a method, device and system for brachytherapy includes multiple atraumatic spacer components for spacing body portions for radiation therapy a safe distance from the distal end of each treatment site in a manner that provides an array that can be readily shaped according to shaping of the location or locations targeted for radiation treatment.

An additional embodiment concerns a system, device and method for radiation therapy where a radiation detector and a radiation data receiver are included. In a particular embodiment, the radiation detector is positioned on or in at least one of a plurality of spacer bubble or elongated balloon components in an array sized, shaped and positioned to provide spacing distance to the body location of radiation therapy delivery. The device is disposable, and can be for single-use only, and in embodiments, the device is readily changed in size such as cut with a scissors, scalpel or other sharp instrument, or separated at lines of weakening.

A further embodiment concerns a system, device and method for radiation therapy which includes a hyperthermia sub-system having a thermal delivery location generally adjacent to a radiation delivery location of the system, device and method. In a particular embodiment, the hyperthermia sub-system is generally adjacent to a radiation delivery location. In a further particular embodiment, the hyperthermia sub-system opens into the radiation delivery location of at least one catheter-like component for radiation source delivery.

Yet a further embodiment concerns a system and method for brachytherapy that includes, in combination, a hyperthermia sub-system and a radiation detector, both positioned in the close vicinity of the radiation delivery location along the catheter-like component. A radiation data receiver is located external of the body within which the brachytherapy is proceeding. Alternatively, the detector may be fixed and its data later able to be analyzed.

These and other aspects, features, improvements and advantages will be understood through a consideration of the following detailed description.

BRIEF DESCRIPTION OF THE DRAWINGS

In the course of this description, reference will be made to the attached drawings, where incorporated.

FIG. 11 is an alternate embodiment of the distal-most surface of the device showing a plurality of gas-filled protrusions in the nature of bubbles that engage the body being treated;

FIG. 12 is a cross-section through the line 12-12 of FIG. 8;

FIG. 13 is a further embodiment wherein a single radiation delivery tube feeds all radiation treatment sites of this embodiment;

FIG. 14 is a top plan view and additional embodiment of a treatment device having a radiation delivery tube for each radiation site of the sheet-like member;

FIG. 15 is a perspective view of an additional embodiment that is in the nature of a mitt version of sheet-like member for delivery radiation to a sarcoma or the like;

FIG. 16 is a perspective view of a glove-styled sheet-like member having a plurality of bubbles spacing radiation treatment termini of the device, this view being the patient engagement side;

FIG. 17 is a perspective view opposite the patient-engagement side shown in FIG. 16, illustrating a plurality of treatment tubes;

DESCRIPTION OF THE ILLUSTRATED EMBODIMENTS

The embodiments disclosed herein are exemplary only, and the subject matter described herein may be embodied in various forms. Therefore, specific details described herein are not to be interpreted as limiting the subject matter as defined in the accompanying claims.

Figure 1:
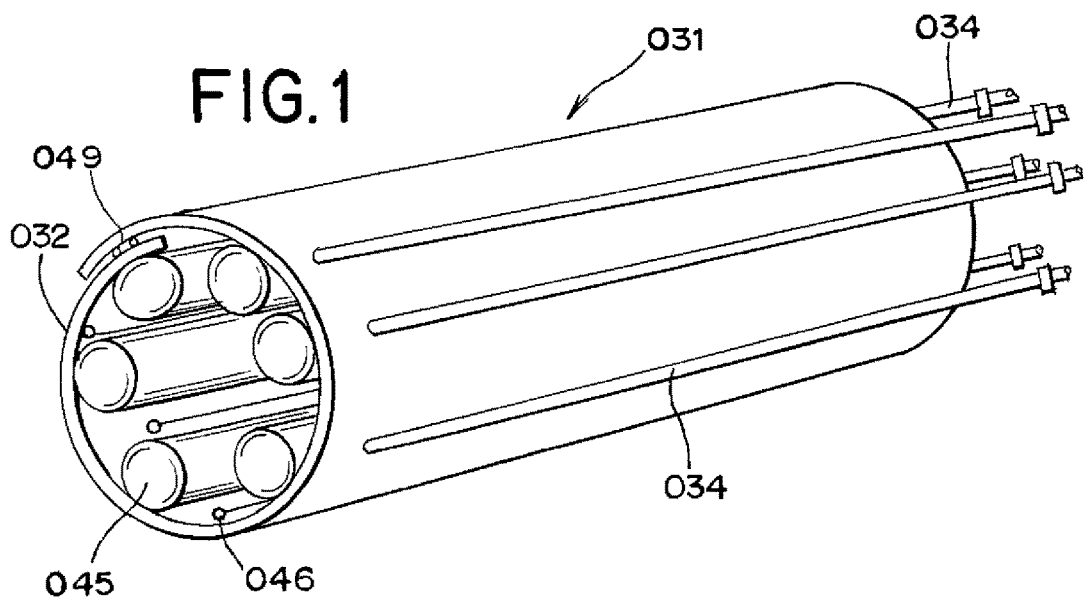
FIG. 1 is a perspective view of an embodiment of a sheet-like radiation treatment device that is wrappable generally over elongated balloons of the device.
Figure 1A:
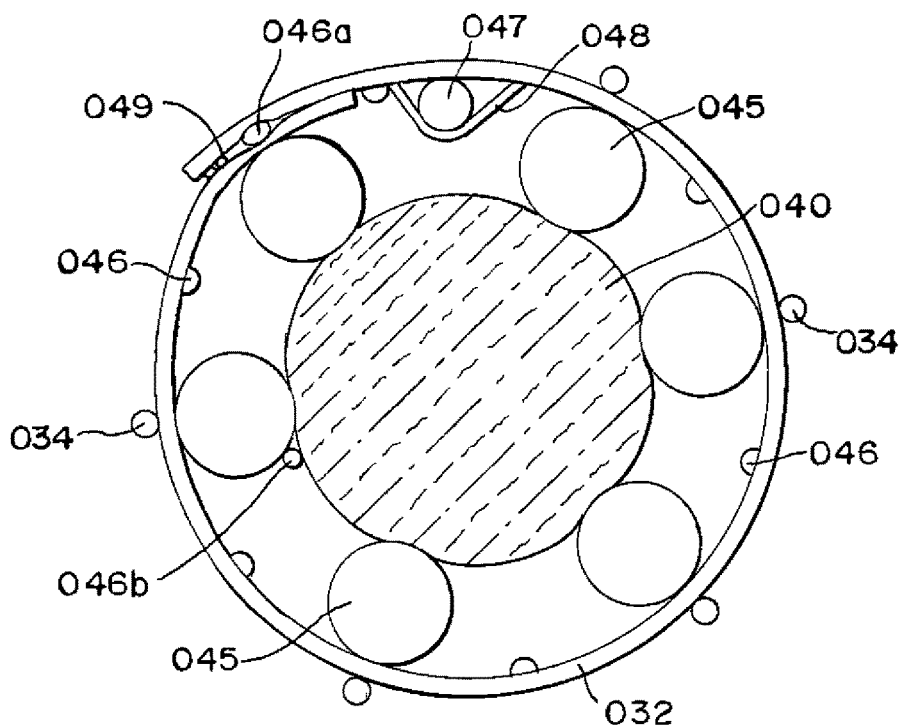
FIG. 1A is an end view of a device similar to that of FIG. 1, shown wrapped around and secured to a body limb, such as an arm, leg, finger or toe.

The sheet-like member illustrated in FIG. 1, generally designated at 031, has a support 032 that is generally rectangular in its perimeter when laid out flat. As seen in FIG. 1 and FIG. 1A, the sheet-like member is folded or rolled onto itself, forming an open volume therewithin. Support 032 is made of tough and flexible polymeric material that is biocompatible. From this, it will be appreciated support 032 is shaped, sized and constructed of material that allows flexibility of the sheet-like device 031 while providing strength adequate to maintain the integrity of the device and the other components of same. The flexibility is adequate, for example, to wrap around a body limb such as an arm, leg, finger or toe. The flexibility also is adequate to wrap over or within a surgically opened sarcoma or other cancerous area within the body of the patient. The flexibility also can be suitable for placing on or within typically gentler torso curves or surgically exposed torso walls or internal sarcoma sites, including for a retroperitoneum treatment As perhaps best seen in FIG. 1A, the sheet-like member is especially easily and conveniently applied over a body limb, shown in cross-section at 040. A plurality of elongated balloons 045 are shown in an array along one face of the sheet-like member. In this embodiment, the balloons 045 extend substantially the full length of the sheet-like member, although they can be shorter in length and not cover the entire length of the sheet-like member, or they can be shorter in length and placed in spaced relationship to each other. They can be lined up end-to-end, or they can be staggered along all or a portion of the surface of the sheet-like member. Balloons 045 often will be substantially filled with air being sealed therewithin; alternatively, the balloons can be inflatable. However, in any event, it is important for the balloons to perform the function of an atraumatic spacer between the radiation energy delivery location or locations and the target area of the patient to be treated with radiation therapy.

The opposing surface of the support 032 receives a plurality of delivery tubes 034. The delivery tubes can be a few inches in length, such as about eight inches, or they can be of an extended length, such a about three feet or one meter. Shorter length tubes 034 are sized, shaped and adapted to securely connect with delivery hoses of radiation isotope delivery devices known in the art. The longer delivery tubes 034 may be more flexible than the shorter delivery tubes, at least in part, for safe and secure connection to a suitable isotope delivery unit known in the art. In this embodiment, each delivery tube 034 is longitudinally oriented on the surface of the support 032 that is opposite the surface on which the balloons 045 are positioned.

A plurality of detectors 046 are positioned on the device. Microdiodes are illustrated, along with wires to electronic connection to a suitable monitor and/or processor of a type generally known in the art. Detectors can be in wireless electronic connection as well, as desired. Also shown is a detector 046a at a location in line with one of the balloons but on the opposite surface of the sheet-like member 032. Detectors can also be positioned within the thickness of the sheet-like member, as well as on its inside or outside surface. Detectors also can be positioned directly on the balloons. For example, if the magnitude of radiation at the interface between the spacer balloon and the body member being treated, such as an arm, the detector can be at a location engaging or very closely spaced from the body member, such as the detector 046*b*.

A hyperthermia delivery tube 047 can be provided on a surface of, or within the sheet-like member 032. Attachment can be by passing through a loop or holder 048 on the sheet-like member. Alternatively, the hyperthermia tube can be unattached to the sheet-like member itself and be insertable as desired for hyperthermia treatment and effects desired by the medical professional applying the device during radiation therapy.

When the sheet-like device 031 is used as illustrated in FIG. 1 and FIG. 1A, an attachment means 049 will ensure that the rolled configuration will be maintained during treatment. A typical attachment means is a hook and loop combination as well-known in the art. Others include snaps, mating profile zip strips, spear-and-grommet pairs, pressure-sensitive adhesives, tacky adhesives with peel strips, moisture-responsive adhesives, glues and the like.

Figure 2:
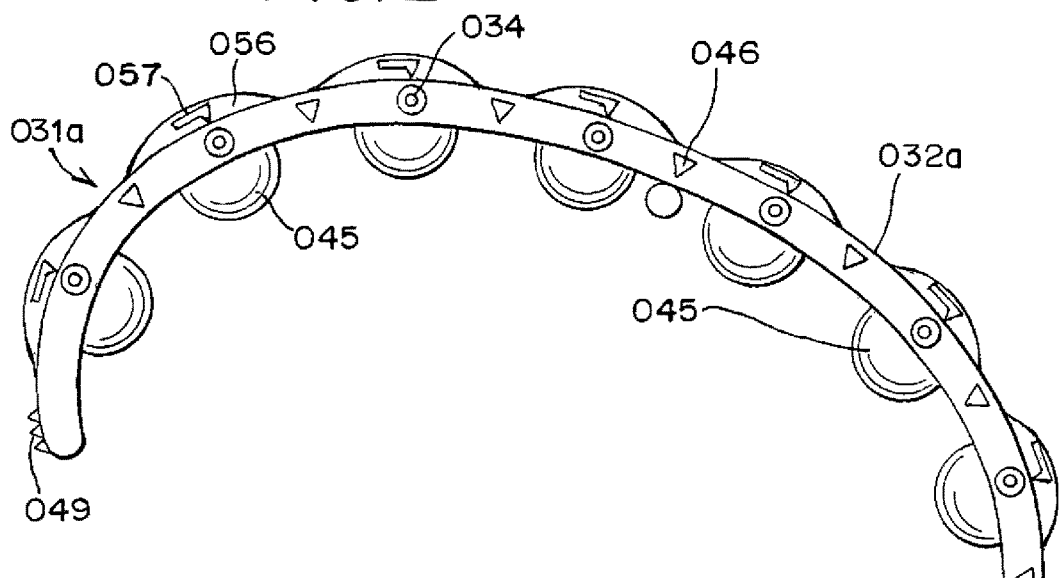
FIG. 2 is an end view of a further embodiment of a sheet-like radiation treatment device that is flexible in a direction generally transverse to a plurality of elongated balloons, and including a plurality of inflatable balloons, shown in deflated condition.
Figure 2A:
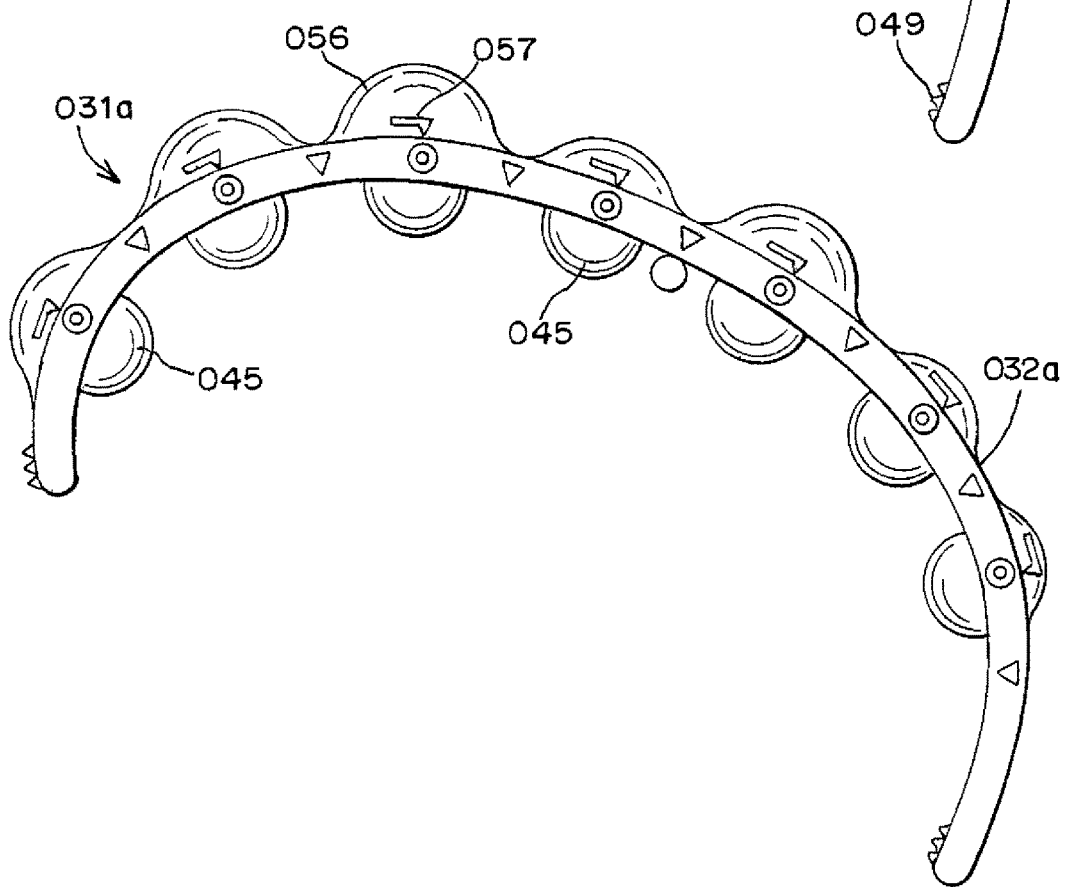
FIG. 2A is an end view of the embodiment of FIG. 2, shown with the inflated balloons in different degrees of inflation.

The sheet-like member illustrated in FIG. 2 and FIG. 2A, generally designated at 031*a*, has a support 032*a* has a perimeter that can be rectangular, square, long and narrow, narrow and long, in parallelogram configuration, rhomboidal, oval, circular, five-sided, or hexagonal. Support 032 is shaped, sized and constructed of material that allows flexibility of the sheet-like device 031 while providing strength adequate to maintain the integrity of the device and the other components of same. The flexibility is adequate, for example, to wrap around a body limb or surgically opened body limb. The flexibility also can be suitable for placing on typically gentler torso curves or surgically exposed torso walls or internal sarcoma sites.

This embodiment includes a plurality of inflatable elongated balloons or non-elongated bubbles 056, each having an inflation passageway 057. The inflatable members 056 are in their deflated or non-inflated condition as shown in FIG. 2, and each is shown at a different level of inflation in FIG. 2A. These inflatable members 056 are useful in adding comfort to the patient, particularly when the device 031 is positioned within a body cavity or a surgically opened body location. Also, the inflatable members are useful in moving away, pushing and/or protecting body portions, especially body portions not desired to be treated during the particular radiation therapy regimen prescribed. Because each inflatable member 056 is individually controlled, it is possible to tailor the cushioning or pushing function along the surface of the device. When desired, it is also possible to have the inflation passageways 057 interconnected so each inflatable member 056 will inflate or deflate to about the same degree when inflation fluid such as saline solution or air are added or removed from the passageways 057.

Figure 3:
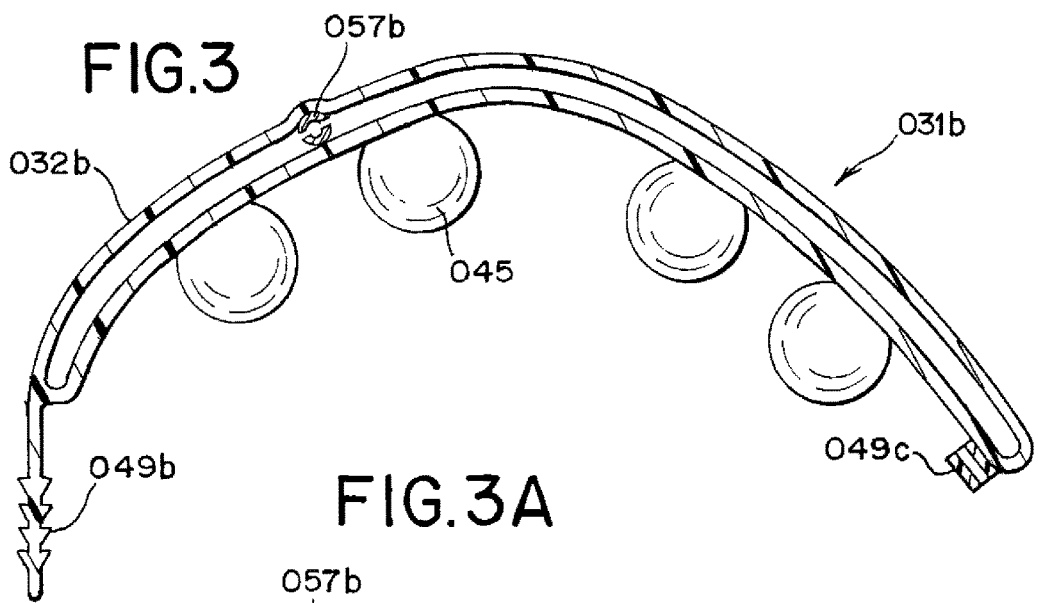
FIG. 3 is a cross-sectional view of another embodiment, including an inflatable flexible support.
Figure 3A:
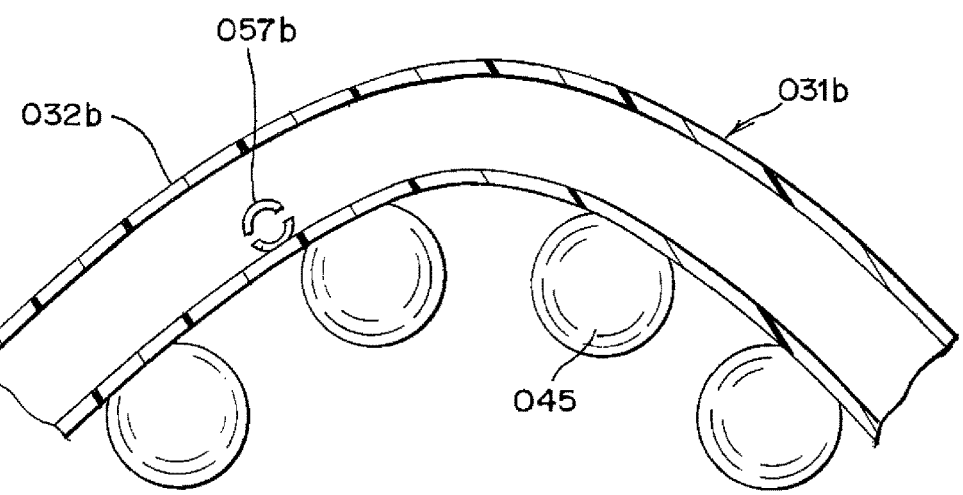
FIG. 3A is a cross-sectional view of the embodiment of FIG. 3, shown in an inflated condition.

The sheet-like member illustrated in FIG. 3 and FIG. 3A, generally designated at 031*b*, has a support 032*b* that is shaped, sized and constructed of material that allows flexibility of the sheet-like device 031*b* while providing strength adequate to maintain the integrity of the device and the other components of same. The flexibility is adequate, for example, to wrap around a body limb or surgically opened body limb. The flexibility also can be suitable for placing on typically gentler torso curves or surgically exposed torso walls or internal sarcoma sites, for example. In this embodiment, the support 032*b* itself is inflatable in order to provide a function similar to that of the inflatable members 056. Inflation and deflation are achieved through the passageway 057*b*. FIG. 3 shows attachment means in the form of a spear 049*b* and grommet 049*c* that received the spear allowing adjustability depending on depth of spear insertion.

Figure 4:
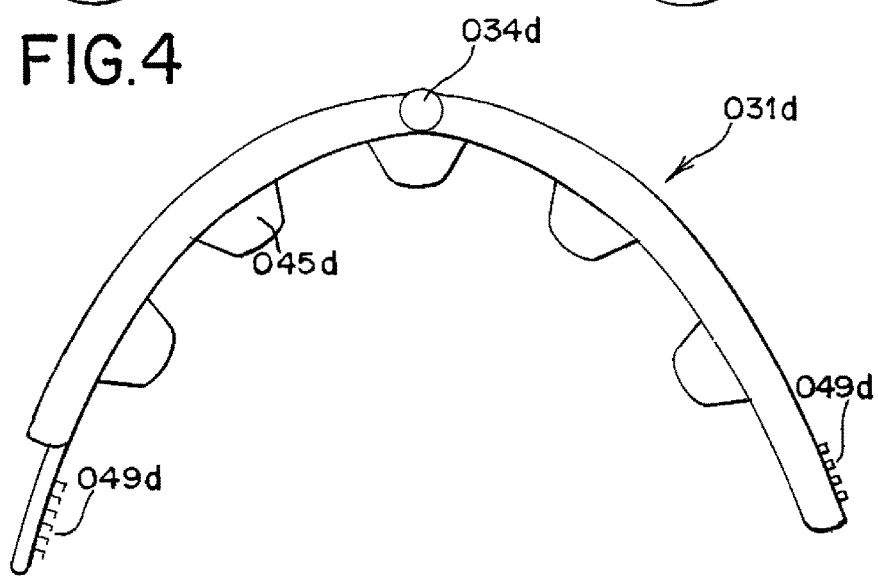
FIG. 4 is an elevational view of an additional embodiment of a flexible sheet device incorporating atraumatic spacers.

The sheet-like member illustrated in FIG. 4, generally designated at 031*d*, has a support 032*d* that is shaped, sized and constructed of material that allows flexibility of the sheet-like device 031*d* while providing strength adequate to maintain the integrity of the device and the other components of same. The flexibility is adequate, for example, to wrap around a body limb or surgically opened body limb. The flexibility also can be suitable for placing on typically gentler torso curves or surgically exposed torso walls or internal sarcoma sites, for example. In this embodiment, a delivery tube 034*d* provides the radiation treatment, and the spacers are atraumatic porous spacers 045*d* which has a noticeable but not extensive compressibility or elasticity, depending on the selected material for same. The material is not expensive and readily disposed and suitable for single-use applications. The illustrated attachment means 049*d* is a pair of opposing and interlocking profiles that can adjust the wrapped length of the device 031*d* depending of which pair is selected for inter-engagement.

Figure 5:
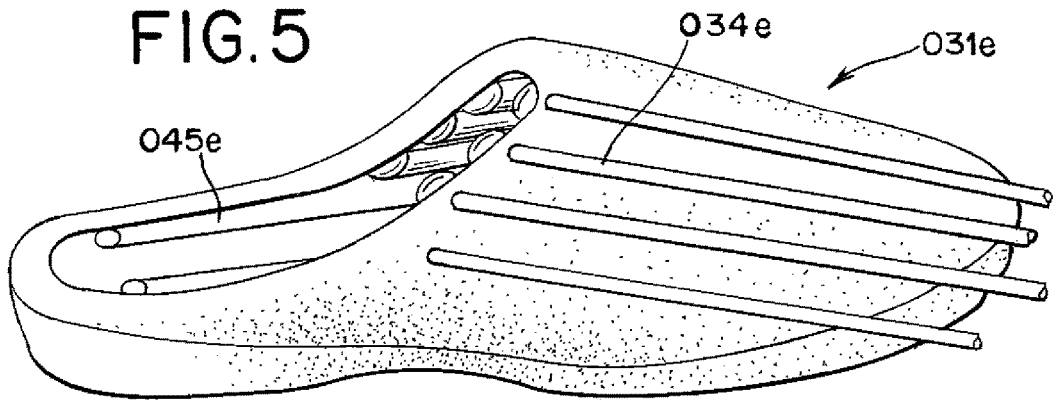
FIG. 5 is a perspective view of an additional embodiment of a sheet-like radiation treatment device that is for treatment of foot cancers.
Figure 6:
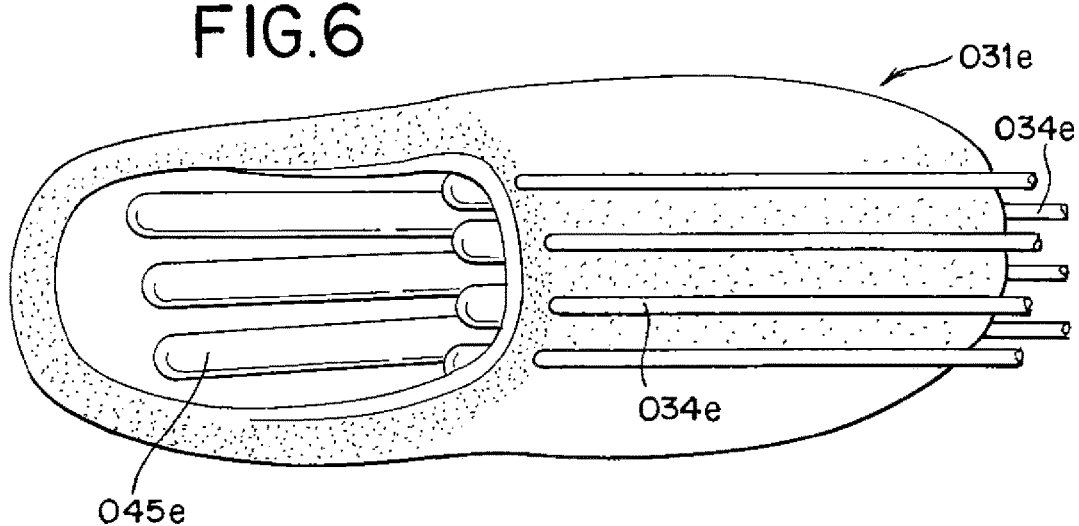
FIG. 6 is a top plan view of the embodiment illustrated in FIG. 5.
Figure 7:
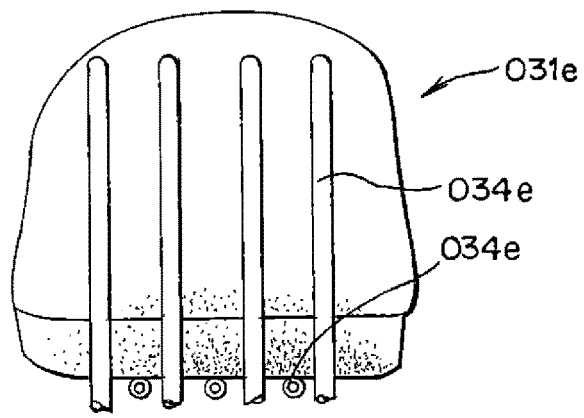
FIG. 7 is a front elevation view of the embodiment illustrated in FIG. 5 and FIG. 6.

The sheet-like member illustrated in FIG. 5, FIG. 6 and FIG. 7, generally designated at 031*e*, has a support 032*e* that is in the general shape of a piece of footwear, such as a clog, slipper, shoe or the like. Same is made of an inexpensive material that is suitable for disposal and intended primarily for one-time usage. Support 032*d* is shaped, sized and constructed of material that allows flexibility while retaining the general shape of footwear so same will remain comfortably in place when treating a foot, portion thereof, such as toe or instep, with radiation material as generally discussed herein, and while providing strength adequate to maintain the integrity of the device and the other components of same.

A plurality of elongated balloons 045*e* are shown in an array along one face of the sheet-like member. In this embodiment, the balloons 045*e* extend substantially the full length of the inner surfaces on the top or instep part of the device, as well as on the inner surface of the bottom or heel and sole part of the device. The balloons 043*e*, although they can be shorter in length and not cover the entire length of the instep or sole and heel area, or they can be shorter in length and placed in spaced relationship to each other. They can be lined up end-to-end, or they can be staggered along all or a portion of the surface of the sheet-like member. Balloons 045*e* often will be substantially filled with air being sealed therewithin; alternatively, the balloons can be inflatable. However, in any event, it is important for the balloons to perform the function of an atraumatic spacer between the radiation energy delivery location or locations and the target area of the patient to be treated with radiation therapy.

The outer surfaces of the instep and heel and sole of the support 032*e* receive a plurality of delivery tubes 034*e*. The delivery tubes can be a few inches in length, such as about eight inches, or they can be of an extended length, such a about three feet or one meter. Shorter length tubes 034*e* are sized, shaped and adapted to securely connect with delivery hoses of radiation isotope delivery devices known in the art. The longer delivery tubes 034*e* may be more flexible than the shorter delivery tubes, at least in part, for safe and secure connection to a suitable isotope delivery unit known in the art. In this embodiment, each delivery tube 034*e* is longitudinally oriented on the indicated outer surfaces of the support 032*e* that is opposite the surfaces on which the balloons 045*e* are positioned.

Figure 8:
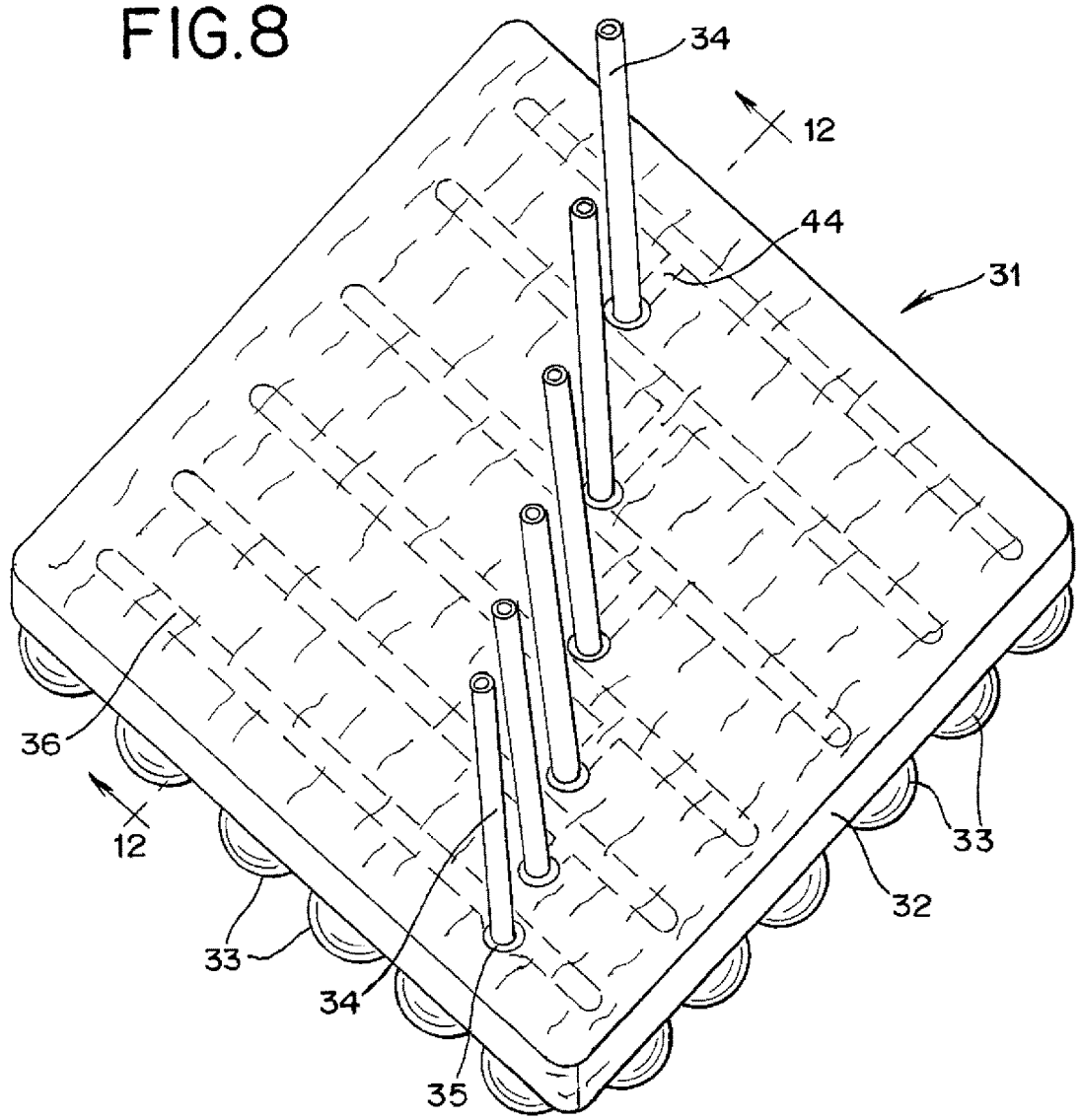
FIG. 8 is a perspective view of a further embodiment of a sheet-like radiation treatment device with multiple delivery tubes feeding different groupings of treatment sites.

The sheet-like member illustrated in FIG. 8, generally designated at 31, has a support 32 that is generally rectangular in its perimeter. Support 32 is shaped, sized and constructed of material that allows flexibility of the sheet-like device 31 while providing strength adequate to maintain the integrity of the device and the other components of same. The flexibility is adequate, for example, to wrap around a body limb or surgically opened body limb. The flexibility also can be suitable for placing on typically gentler torso curves or surgically exposed torso walls or internal sarcoma sites.

The sheet-like device 31 further includes a plurality of balloons or bubbles 33 on a distal-most surface of the support 32. The opposing surface of the support 32 receives a plurality of delivery tubes 34, these being generally oriented normal to the support 32. The delivery tubes can be a few inches in length, such as about eight inches, or they can be of an extended length, such a about three feet or one meter. Shorter length tubes 34 are sized, shaped and adapted to securely connect with delivery hoses of isotope delivery devices known in the art. The longer delivery tubes 34 may be more flexible than the shorter delivery tubes, at least in part, for safe and secure connection to a suitable isotope delivery unit known in the art.

A securement member 35, such as a grommet that secures the delivery tube 34 to the support 32. In this particular embodiment, a plurality of elongated balloons or otherwise-shaped bubbles 33 are in a group (of six in this embodiment) being operatively connected by a channel 36 of the support 32. The channel receives isotope material, such as seeds, from the delivery tube for distribution at a terminus site corresponding to each balloon or bubble 33. Although not explicitly shown in FIGS. 8-25 detectors and hyperthermia members are included in embodiments and for the reasons and objectives as generally noted herein.

The balloon or bubble 33 has a depth (for example 1 cm) due to its inflated condition and when positioned on the patient. In a typical embodiment, each balloon or bubble 33 is sealed and contains air or other gas or fluid that will maintain the desired spacing prior to and during treatment.

Figure 9:
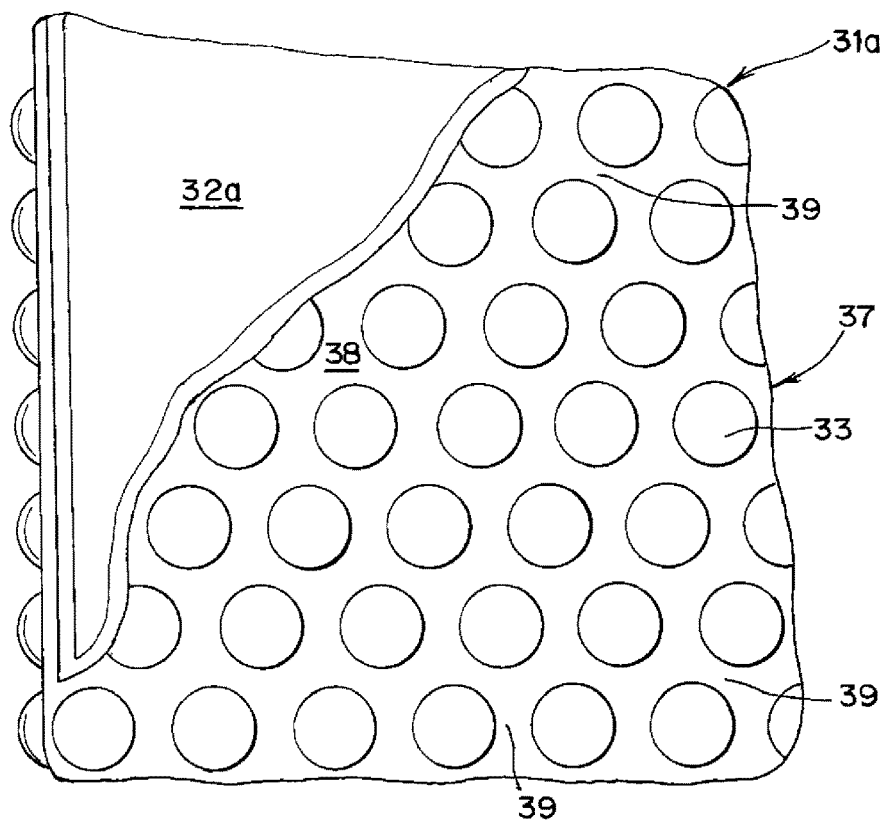
FIG. 9 is a detailed perspective view, partially broken away of the device of FIG. 8 from which the delivery tubes and a portion of the support are removed.
Figure 10:
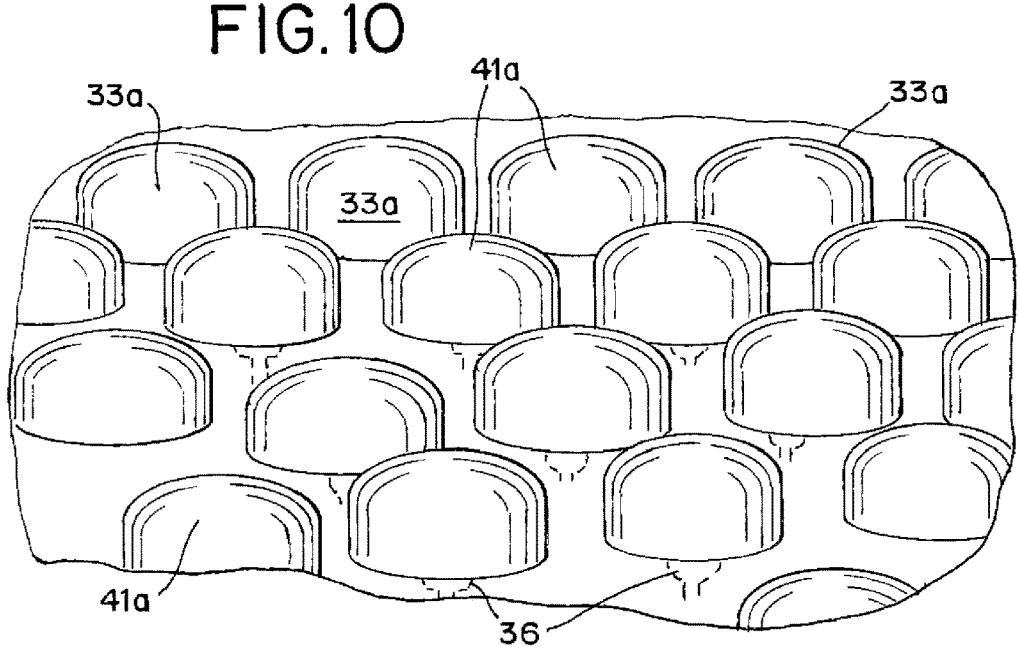
FIG. 10 is a detailed view of the undersurface of the device of FIG. 8 showing a plurality of inflated bubbles that engage the body surface being treated.

A typical embodiment of the balloons or bubbles 33 is depicted in FIG. 9 and FIG. 10. In FIG. 9, the sheet-like device is shown with the support 32 and other components removed, at least partially. When the support 32 is a backing assembled onto a bubble array layer, generally designed at 37, the support 32 and bubble array layer 37 each contain flat surfaces from which the bubbles 33 protrude in a direction away from the support 32. In the FIG. 9 embodiment, the bubble array layer is in the form of a flexure panel 38 that includes ridges 39 between bubbles 33.

Alternatively, as generally illustrated in FIG. 8, the support 32, bubbles 33 and flexure panel 38 and ridges 39 are molded as a single unit, rather than being an assembly as illustrated in FIG. 9, wherein the support 32a had been made separately from the bubble array layer 37 and assembled thereto by sonic welding, adhesive, glue, heat welding or the like to form the sheet-like device, generally designated at 31a.

FIG. 10 provides a view of the patient-engagement portion of the sheet-like device. In this instance, a large plurality of generally hemi-spherical balloons or bubbles 33a are under low-pressure inflation, which can enhance the comfort level for the patient.

FIG. 11 also is a view of the patient-engagement portion of another embodiment of the sheet-like device 31b. In this instance, the multiple balloons or bubbles 33b are more fully inflated and exhibit a more defined shape than the balloons or bubbles 33a shown in FIG. 10. Such a higher pressure arrangement can be more conducive to maintaining spacing between the engagement surface 41b of each balloon or bubble 33b. The engagement surfaces 41a of the lower pressure balloons or bubbles 33a provides a more pliable interface than engagement surfaces 41b.

Referring to FIG. 12, each balloon or bubble 33 has an engagement surface 41. The channel 36 which receives the radiation treatment isotopes in the form of seeds or the like has a distal terminus 42 that provides the farthest distal location possible for the radiation treatment material and distal terminus 42 that provides the farthest distal location possible for the radiation treatment material. Each distal terminus 42 has a closed end 43 that is spaced from the engagement surface 41 by a distance "D" illustrated in FIG. 12. This is the primary function of the spacer members in all of the embodiments. Distance "D" is typically on an order of 1 cm, depending somewhat upon the intensity of the radiation emanating from the isotope material at the distal terminus 42. It will be appreciated that the depth of each balloon or bubble 33, 33a, 33b, when positioned onto the body surface being treated, provides a well-defined spacing distance between the most distal location of the radiation emanating from the treatment material and the diseased target site of the body. A flexible tube 43 is shown in FIG. 12 for connection to the desired radiation treatment source according to practices known in the art.

As noted, FIG. 8 illustrates the situation where each delivery tube 34 feeds the radiation treatment material to a group of balloons or bubbles 33 by way of a channel 36 for each group, each channel having a plurality of distal termini 42. FIG. 13 illustrates the situation where a single delivery tube 34c feeds multiple channels 36c that run from the delivery tube 34c to each distal terminus 42c. With this approach, a single delivery tube or flexible extension tube is connected to the radiation source.

FIG. 14 shows an embodiment wherein each balloon or bubble 33 has its own delivery tube 34d that is generally positioned directly in line with the distal terminus spaced from each balloon or bubble 33 by the distance "D". With this approach, it is possible for the radiation oncologist or other medical professional to tailor the radiation treatment associated with each balloon or bubble. For example, where a portion of a living body that is overlain by the sheet-like device has no evidence of disease, the medical professional might map the treatment so that no radiation therapy material is delivered to the distal terminus 42d for that particular balloon or bubble. For other sites, as a further example, a more aggressive radiation material loading would be delivered to the distal terminus 42d spaced from the balloon or bubbles to engage such an area. An intermediate gradient between these two extremes can, with this approach, be mapped so as to very closely tailor treatment for a particular sarcoma or the like.

The approach illustrated in FIG. 8 and FIG. 12 also provide tailoring options, but to a more limited extent. The amount of radiation treatment delivered or not delivered into a tube 34 will modify delivery into each individual channel 36 and each distal terminus 42 along that channel. FIG. 8 also illustrates another opportunity for variability in treatment at individual bubbles within the groups of bubbles 33, depending upon the placement of the delivery tube 34 along the length of the channel 36 that is fed by the particular tube. When a treatment material is used that is not regularly flowable, the amount of radiation treatment emanating from the distal termini 42 along a particular channel 34 can depend upon the distance between each distal terminus and the entry path 44 between the distal end portion of the tube and its channel. For the entry path 44 is closely spaced from a particular bubble's opposing distal terminus, it can be possible to provide more intense treatment than a distal terminus separated from the entry path 44 by a greater distance.

FIG. 15 shows another embodiment in which a plurality of sealed and inflated semi-spherical balloons or bubbles are not directly associated with a distal terminus for radiation treatment; instead, multiple balloons or bubbles provide the spacing function of balloons 33, 33a, 33b of other embodiments, and a distal terminus or multiple distal termini are positioned on the support from which the multiple balloons or bubbles protrude away from.

The particular embodiment of FIG. 15 includes a support and balloon or bubble combination that is more on the order of package cushioning material, sometimes referred to as "bubble wrap". Sheet-like device, generally designated at 51, shows multiple bubbles 53 on a flexible support 52. A delivery tube or catheter 54 delivers the radiation dose along its length that generally corresponds to the length of the sheet-like device 51. Delivery tube or catheter 54 connects to a flexible extension tube 43 or is itself long enough to be connected to a source of radiation treatment material in order to allow delivery of material to the distal end portion of the delivery tube or catheter 54.

In the embodiment of FIGS. 16 and 17, the sheet-like device takes the form of a glove-like device, generally designated 61. The support is somewhat glove-like in shape, being designated 62. FIG. 16 shows patient-engaging side with multiple balloons or bubbles 63 inside the device and includes a branched catheter or delivery tube 64 for delivering radiation treatment material to the glove-like device 61, to which the catheter is secured by anchor members 60. Delivery of the radiation material along the catheter or delivery tube, particularly at its distal end portion branches 59, proceeds in a manner similar to that described with respect to other embodiments hereof, such as FIG. 1.

Figure 18:
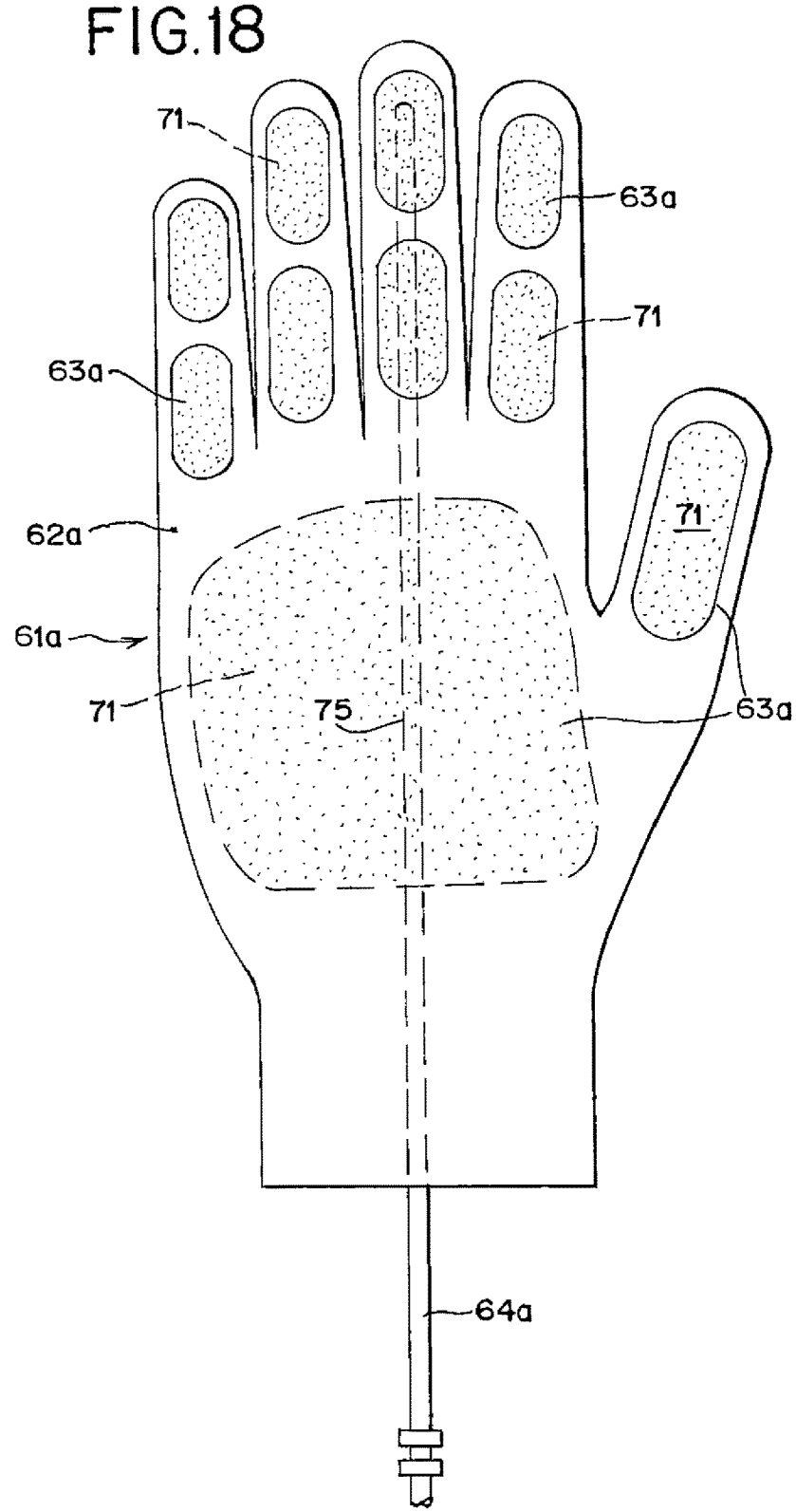
FIG. 18 is a plan view of a further embodiment having spacing balloons or bubbles on each digit and on the palm of this glove-styled sheet-like member.
Figure 19:
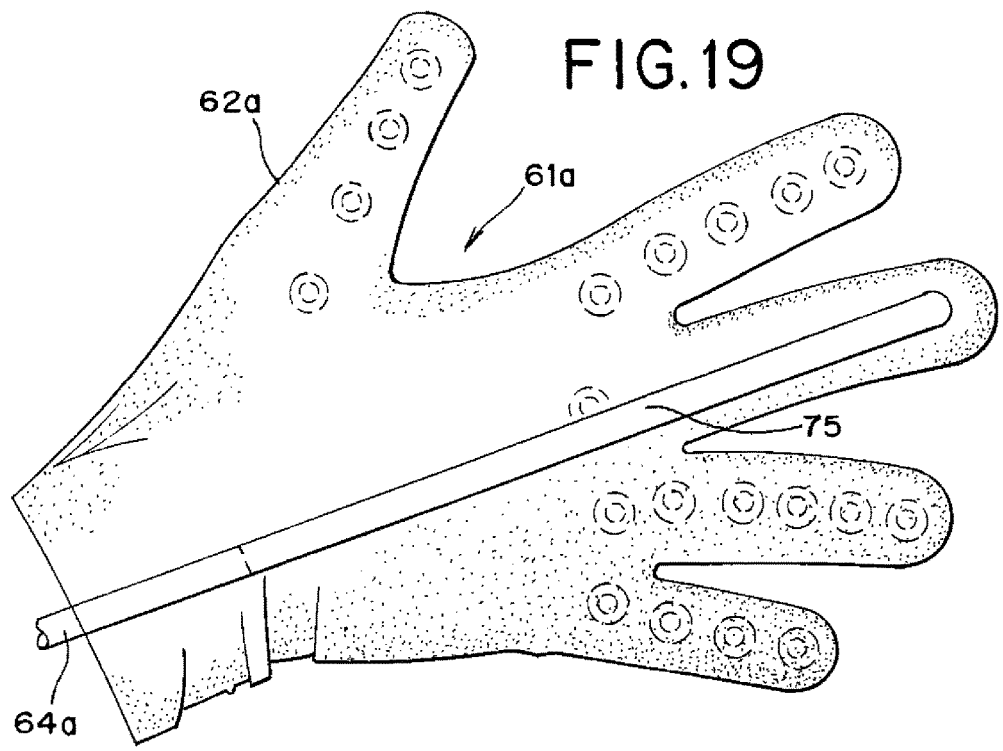
FIG. 19 is a plan view of the "backhand" side of the embodiment illustrated in FIG. 18.

FIG. 18 includes a plurality of elongated balloons or bubbles 63a which also are on the inside surface of a glove-like support 62a. A delivery tube catheter 64a has a distal end portion 75 that delivers radiation treatment spaced from the engagement surface 71 of each balloon or balloons. FIG. 19 illustrates a "back hand" view of the FIG. 18 embodiment.

Figure 20:
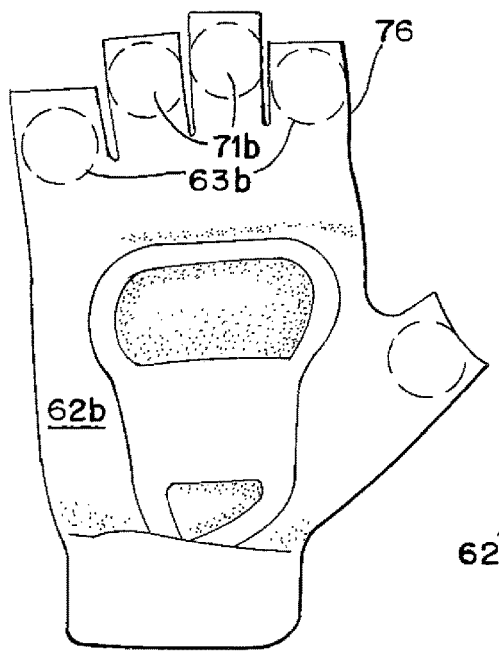
FIG. 20 is a plan view of a an additional embodiment of a treatment device having open-ended finger and thumb channels, this being the patient-contacting side.
Figure 21:
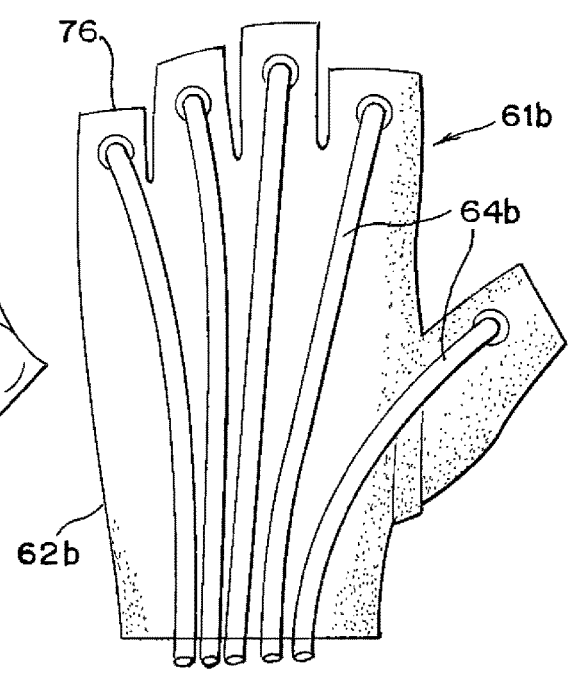
FIG. 21 is a plan view of the embodiment of FIG. 20, showing the side of the device of this embodiment facing away from the patient.

FIG. 20 and FIG. 21 illustrate a sheet-like device that is a glove-like sleeve device 61b having truncated finger-like members 76 that can have open ends if desired. A plurality of balloons or bubbles 63b are shown, each having an engagement surface 71b inside the device 61b. A support 62b has provided multiple catheter or delivery tubes 64b are capable of delivering the radiation treatment material to one or more of the digital locations.

Figure 22:
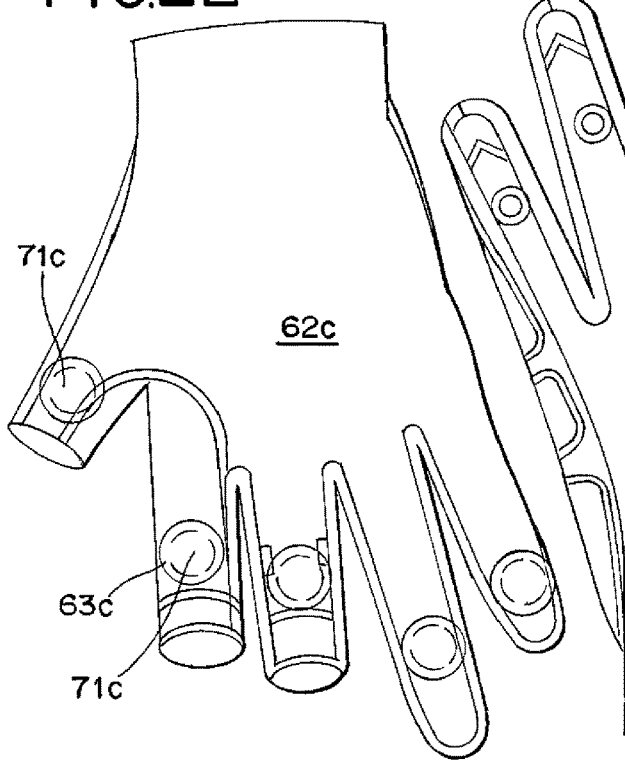
FIG. 22 is a generally perspective view of an added embodiment of the patient-engaging portion of the device, which has a combination of closed and open digit receptor channels.
Figure 23:
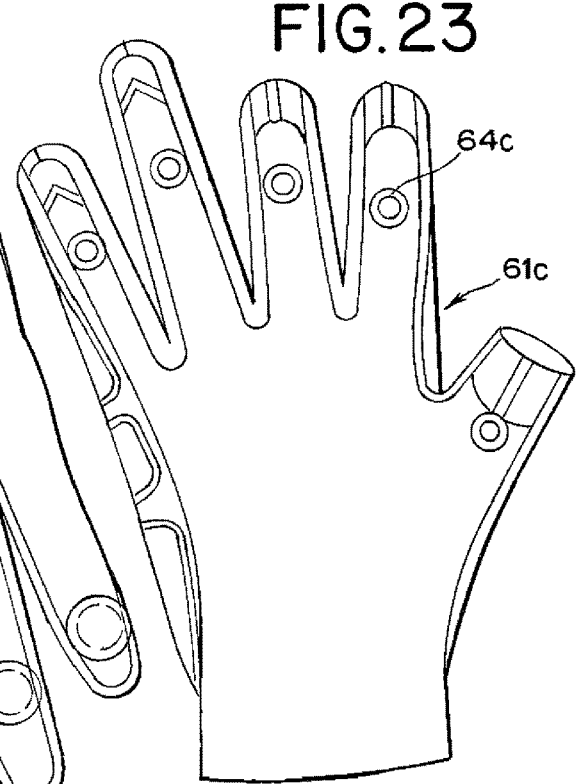
FIG. 23 is a generally perspective view of the embodiment of FIG. 22, taken from the side opposite of the patient engagement side.

FIG. 22 and FIG. 23 show an arrangement of a sheet-like member on the order of FIG. 20 and FIG. 21, with the combination of an open-ended digit combination embodiment which is a glove-like device 61c having a support 62c from which a plurality of balloons or bubbles 63c protrude, each having an engagement surface 71c. In this embodiment, catheter or delivery tubes 64c projects in a direction away from the balloons or bubbles.

Figure 24:
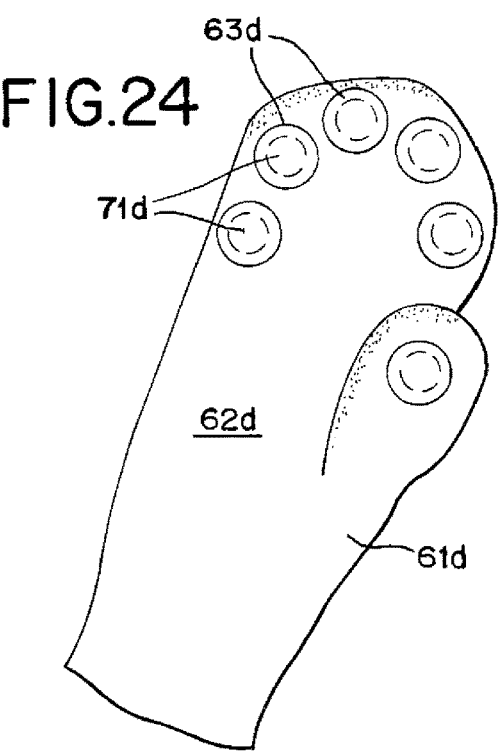
FIG. 24 is a plan view of a mitten-style sheet-like device, shown from the patient-engaging side.
Figure 25:
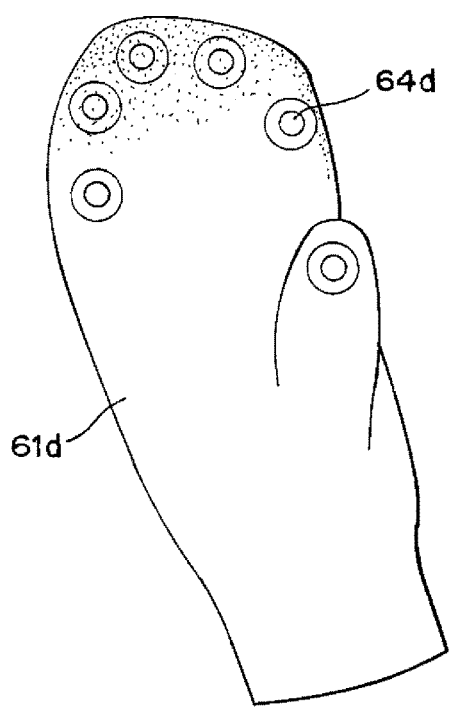
FIG. 25 is a plan view of the side of the FIG. 24 embodiment that is opposite of the patient-engaging side.

In FIG. 24 and FIG. 25, the sheet-like member is a glove-like device 61d without the multiple digits of other embodiments but is otherwise similar to FIG. 22 and FIG. 23. Support 62d has protruding therefrom a plurality of balloons or bubbles 63d, each having an engagement surface 71d. Catheter delivery tube 64d is illustrated.

Typical delivery tubes 34, 034 and so forth are elongated treatment members that can be considered treatment rods, and when in treatment mode they contain small radioactive pellets or seeds which irradiate diseased tissue. In some embodiments, these rods have a lumen or lumens to accept the radioactive material, whether solid, liquid or gaseous. The size, dose rate and spacing of these radioactive sources such as seeds or pellets are prescribed by the physician and assembled prior to and/or during the procedure in which the catheter device is ready for insertion through the body cavity orifice and into the body cavity.

Different embodiments can utilize one or more different approaches to secure the delivery tubes to the sheet-like device before and during radiation therapy.

Embodiments can incorporate a Foley-type catheter for radiation therapy in the bladder. When provided, the Foley-type catheter enables the necessary drainage of liquids or gasses, including urine or other body fluids like during the therapeutic procedure without having to move or remove the catheter device.

With further reference to the one or more detectors noted herein, examples are a diode or a microdiode, which facilitate treatment and evaluation of the radiation therapy regimen, typically in association with a hyperthermia treatment. Each detector senses and if desired leads to recordal of dose amounts and an indication of location. Detectors can be imbedded in another component such as a balloon or a catheter, or be positioned on or in such component. In many regimens, it is advantageous to provide detectors in a symmetrical array, for example evenly spaced from each other or from a reference location. Detectors also can be movable and/or removable. Positioning can be anterior, posterior, right plane, left plane, for example.

The balloons or bubbles are typically made of a polymer material, including latex, and body-compatible or medical grade polymers. The balloons or bubbles may be shaped so as to be generally round, oblong, semicircular or curved along one side and flat along another side, such as being generally D-shaped in cross-section. When inflatable, the balloons or bubbles are inflated by means of the inflation tubes noted herein in order to inflate and deflate the support, the balloon or the bubble as desired, which inflation tube and passageway connect with a pressurized fluid source and may include a valve or regulator. The pressurized fluid may be a biocompatible gas such as air or a biocompatible fluid such as saline solution. The means of pressurization may be a pressurized tank, an in-house line plumbed to the treatment room, a hypodermic syringe, or the like.

When desired, the delivery tubes are rendered radio therapeutic by being loaded with radioactive pellets, rice, seeds, wires, fluids or the like, either before or after insertion of the device into the body. Any other suitable member for effecting radiotherapy may be used provided it can be moved into position by the therapeutic balloon. Positioning of the rods may be aided by rod receiving members of the sheet-like device or support member, such as holes, channels, straps or the like. In various embodiments, the multiple elongated members can be embedded within the support wall or affixed to the wall or balloon or bubble or spacer. When desired, same could also be affixed to the balloon by strips, hook and loop combinations, straps or the like.

The device may be inserted into the living body for the therapeutic radiation procedure either prior to or following insertion of the radio therapeutic rods into the rod receiving members. A plurality of detectors can be positioned in general association with the radio therapeutic rods. Detectors in this regard are diodes, microdiodes, mini dosimeters or other data collecting devices that can be used to transmit data for "real time" measurement, observation and/or recordal of such data. For example, radiation data are collected in order to quantify radiation at a specific location along the device. When desired, individual detectors can have their own respective data receptors.

Various embodiments also incorporate a hyperthermia system by which heat can be applied to the cancerous area simultaneously with the radiation treatment, or if desired, in close association in time and location with the radiation treatment imparted with the radiation treatment indicated at a detector. The illustrated hypothermia systems include a delivery tube having a distal end portion. Hyperthermia tubes can be at least partially within the device. When desired, the tubes can be used for low dose (LDR) or high dose (HDR) brachytherapy, e.g. microwave, ultrasound, radiant energy, or other type of method. Wires can be placed in the tubes for delivery with or without radiation, whether simultaneously, pre-irradiation, or post-irradiation.

As a general proposition, chemotherapy materials can be included in conjunction with one or more of the radiation treatment devices described herein. Such delivery can be, for example, practiced by way of delivery tubes such as those shown herein for a hyperthermia function in those instances where separate tubing is desired for chemotherapy delivery. Additionally or alternatively, one or more of the balloons or catheter in some embodiments can have impregnated into, infused onto, coated on, or otherwise carry chemotherapy materials separate and apart from being able to be delivered from the outside after insertion into the body. Chemicals or drugs along these lines can be provided in the form of microspheres or other organically bound or chemically bound substances as alternative chemotherapy or radioactive delivery systems. For example, delivery of Bacillum calmette-guerin (BCG) for bladder cancer treatment can be used. In other embodiments, the substance delivered by any of these means can be useful for pain maintenance, such as analgesic materials and pain or narcotic materials to provide pain relief during procedures, especially when the device protocol requires insertion within the body for extended time periods. These can include delayed release analgesics and the like.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A sheet-like radiation therapeutic device, comprising:
a sheet-like support that is a biocompatible polymer sheet sized, constructed and adapted to be shaped according to a target location within a body cavity or surgically opened body location of a radiation treatment subject for radiation therapy at the target location, the sheet-like support having a first surface and a second surface;
a plurality of spacers on the first surface of the sheet-like support, said spacers each having a target site engagement surface spaced from the first surface of the sheet-like support, the spacers each having an opposing surface that engages the first surface of the sheet-like support, whereby the spacers protrude from the first surface of the sheet-like support, said spacers being in an array exhibiting side-by-side separation between the spacers, said spacers not being connected at their respective target site engagement surfaces, and said spacers being structured and adapted to engage tissue at the target location of the radiation treatment subject;
a tubular member sized, structured and adapted to receive radio therapeutic material having prescribed radioactivity; and
an inflated or inflatable member on and protruding from the second surface of the sheet-like member, said inflated or inflatable member is structured and adapted to engage and manipulate tissue surrounding the target location and protect same, specifically including body portions not to be treated during the radiation therapy.

2. The device of claim 1, further including at least one detector that collects data on radiation at a treatment location of the therapeutic device, the detector being associated with the sheet-like support.

3. The device of claim 2, further including a hyperthermia component that delivers hyperthermia treatment that interacts with delivery of radio therapeutic material by the tubular member, and the data collected by the detector is applied to monitor interaction between the radiation treatment member and the hyperthermia component.

4. The device of claim 2, wherein said sheet-like support has a thickness, and said detector is attached to the sheet-like support on its first surface, its second surface or within the thickness of the sheet-like support.

5. The device of claim 2, wherein said detector is secured to the sheet-like support.

6. The device of claim 1, further including a hyperthermia component that delivers hyperthermia treatment that interacts with delivery of radio therapeutic material by the tubular member.

7. The device of claim 6, wherein the hyperthermia component is of the energy type selected from the group consisting of thermal, microwave, ultrasonic, radiant and combinations thereof, which energy is applied without or with radiation, and if with radiation the energy is applied simultaneously, pre-irradiation or post-irradiation.

8. The device of claim 1, further including a securement member of the sheet-like support, and the securement member secures the tubular member to the sheet-like support.

9. The device of claim 1, wherein said inflated or inflatable member is an inflatable member that is structured and adapted to provide manipulation of the target location within the radiation treatment subject by expansive engagement between the inflatable member and the target location upon inflation of the inflatable member.

10. The device of claim 1, wherein the plurality of spacers are a plurality of longitudinally positioned elongated balloons, and the sheet-like support rolls onto itself to form a generally cylindrical roll with the spacers on its inside surface, a plurality of said tubular members are provided, and at least some of the spacers are adapted to engage a limb of the treatment subject.

11. The device of claim 1, wherein the inflated or inflatable member is a plurality of balloons, a plurality of bubbles, or at least one sheet like member.

12. The device of claim 1, further including a longitudinal passageway being large enough to accommodate excrement or other body fluid or gas flow therethrough during a radiation therapy procedure.

13. The device of claim 1, wherein the first surface or second surface of the sheet-like member has a receiving member that engages and holds the at least one tubular member to receive radio therapeutic material, wherein the receiving member is a loop of material which substantially affixes the at least one tubular member along the sheet-like support, the at least one tubular member includes a radio therapeutic rod, and the loop of material substantially affixes the radio therapeutic rod longitudinally along one or both of said first or second surfaces of the sheet-like support.

14. The device of claim 1, wherein the plurality of spacers are elongated balloons that are substantially longer than wide and are sized, shaped and adapted such that when the sheet-like support is folded or rolled on itself, the elongated balloons are adapted to engage the target location.

15. The device of claim 1, wherein associated with the sheet-like support is an open volume formed by the sheet-like support folded or rolled onto itself.

16. The device of claim 1, wherein the radio therapeutic material is a liquid source of radiation.

17. The device of claim 1, further including a tube, and wherein chemotherapy, analgesic material or a combination thereof is impregnated into, infused into, coated on or carried by the tube, the material being fluid, microspheres, organically bound fluid or microspheres, chemically bound fluid or microspheres, or combinations thereof.

18. The device of claim 1, wherein the plurality of spacers include
  a plurality of generally semi-circular sealed and inflated bubbles each protruding from the first surface of the sheet-like support.

19. The device of claim 1, wherein the plurality of spacers on the first surface of the sheet-like support are assembled onto the first surface of, or molded with, the sheet-like support.

20. A sheet-like device for radiation therapy of a target location within a radiation treatment subject for radiation therapy at the target location, comprising:
  a flexible sheet-like support that is a biocompatible polymer sheet sized, shaped and adapted to fold or roll onto itself into a generally cylindrical shape, the support having a first surface and a second surface;
  a plurality of spacers on and protruding from the first surface of the flexible sheet-like support, said spacers each having a target site engagement surface spaced from the first surface of the sheet-like support, said spacers being in an array exhibiting side-by-side separation between the spacers, and said spacers are not connected at their respective target site engagement surfaces;
  the first surface is the interior surface of the sheet-like device of generally cylindrical shape, and the second surface is the outer surface of the sheet-like device;
  at least one tubular member sized, structured and adapted to receive radio therapeutic material having prescribed radioactivity, the tubular member being outside of the second surface of the sheet-like device; and
  whereby the plurality of spacers of the interior surface are structured and adapted to engage a limb of the treatment subject.

21. The device of claim 20, wherein the plurality of spacers on the first surface of the sheet-like support are assembled onto the first surface of, or molded with, the sheet-like support.

* * * * *